US008632845B2

(12) United States Patent
Chen et al.

(10) Patent No.: US 8,632,845 B2
(45) Date of Patent: Jan. 21, 2014

(54) METHOD OF DRYING BIOABSORBABLE COATING OVER STENTS

(75) Inventors: Yung-Ming Chen, Cupertino, CA (US); Jason Van Sciver, Los Gatos, CA (US); Syed F. A. Hossainy, Hayward, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 750 days.

(21) Appl. No.: 12/766,758

(22) Filed: Apr. 23, 2010

(65) Prior Publication Data

US 2010/0323093 A1 Dec. 23, 2010

Related U.S. Application Data

(60) Continuation-in-part of application No. 10/856,984, filed on May 27, 2004, now Pat. No. 7,807,211, which is a continuation-in-part of application No. 10/603,794, filed on Jun. 25, 2003, now Pat. No. 7,682,647, application No. 12/766,758, which is a continuation-in-part of application No. 10/108,004, filed on Mar. 27, 2002, said application No. 10/856,984 is a continuation-in-part of application No. 10/304,360, filed on Nov. 25, 2002, now abandoned, which is a division of application No. 09/751,691, filed on Dec. 28, 2000, now Pat. No. 6,503,556, said application No. 10/856,984 is a continuation-in-part of application No. 10/751,043, filed on Jan. 2, 2004, now abandoned, which is a continuation of application No. 09/750,595, filed on Dec. 28, 2000, now Pat. No. 6,790,228, application No. 12/766,758, which is a continuation-in-part of application No. 12/363,538, filed on Jan. 30, 2009, now Pat. No. 8,007,858, which is a continuation of application No. 10/040,538, filed on Dec. 28, 2001, now Pat. No. 7,504,125, which is a continuation-in-part of application No. 09/894,293, filed on Jun. 27, 2001, now abandoned, which is a continuation-in-part of application No. 09/844,522, filed on Apr. 27, 2001, now Pat. No. 6,818,247.

(51) Int. Cl.
*B05D 3/04* (2006.01)
*A61F 2/06* (2013.01)

(52) U.S. Cl.
USPC ....... 427/2.24; 427/2.1; 427/2.25; 427/372.2; 623/1.42; 623/1.46

(58) Field of Classification Search
USPC ............. 427/2.1, 2.24, 2.25, 372.2; 623/1.42, 623/1.46
See application file for complete search history.

(56) References Cited

U.S. PATENT DOCUMENTS

| | | | |
|---|---|---|---|
| 4,269,713 | A | 5/1981 | Yamashita et al. |
| 4,323,524 | A | 4/1982 | Snowden |

(Continued)

FOREIGN PATENT DOCUMENTS

| | | |
|---|---|---|
| WO | WO 00/42949 | 7/2000 |
| WO | WO 02/058753 | 8/2002 |

(Continued)

OTHER PUBLICATIONS

EPO Examination Report for application 04 812 597.5-2307, mailed Feb. 26, 2007, 2 pgs.

(Continued)

*Primary Examiner* — Cachet Sellman
(74) *Attorney, Agent, or Firm* — Squire Sanders (US) LLP (57) ABSTRACT

Various embodiments of methods for coating stents are described herein. Applying a composition including polymer component and solvent to a stent substrate followed by exposing the polymer component to a temperature equal to or greater than a Tg of the polymer component is disclosed. Repeating the applying and exposing one or more times to form a coating with the result that the solvent content of the coating after the final exposing step is at a level suitable for a finished stent is further disclosed.

17 Claims, 4 Drawing Sheets

(56) References Cited

U.S. PATENT DOCUMENTS

| | | | |
|---|---|---|---|
| 4,839,055 A | 6/1989 | Ishizaki et al. | |
| 5,272,012 A | 12/1993 | Opolski | |
| 5,383,928 A | 1/1995 | Scott et al. | |
| 5,464,650 A | 11/1995 | Berg et al. | |
| 5,468,253 A | 11/1995 | Bezwada et al. | |
| 5,575,818 A | 11/1996 | Pinchuk | |
| 5,651,174 A | 7/1997 | Schwartz et al. | |
| 5,700,286 A | 12/1997 | Tartaglia et al. | |
| 5,733,327 A * | 3/1998 | Igaki et al. | 623/1.5 |
| 5,795,318 A | 8/1998 | Wang et al. | |
| 5,824,048 A * | 10/1998 | Tuch | 128/898 |
| 5,824,049 A | 10/1998 | Ragheb et al. | |
| 5,869,127 A | 2/1999 | Zhong | |
| 5,891,507 A * | 4/1999 | Jayaraman | 427/2.25 |
| 5,897,911 A | 4/1999 | Loeffler | |
| 5,961,914 A | 10/1999 | Mannion et al. | |
| 5,968,091 A * | 10/1999 | Pinchuk et al. | 623/1.16 |
| 5,968,092 A | 10/1999 | Buscemi et al. | |
| 5,980,564 A | 11/1999 | Stinson | |
| 6,056,906 A | 5/2000 | Werneth et al. | |
| 6,066,156 A | 5/2000 | Yan | |
| 6,083,257 A | 7/2000 | Taylor et al. | |
| 6,083,534 A | 7/2000 | Wallach et al. | |
| 6,100,346 A | 8/2000 | Jamiolkowski et al. | |
| 6,139,573 A | 10/2000 | Sogard et al. | |
| 6,146,688 A | 11/2000 | Morgan et al. | |
| 6,153,252 A | 11/2000 | Hossainy et al. | |
| 6,165,212 A | 12/2000 | Dereume et al. | |
| 6,221,102 B1 | 4/2001 | Baker et al. | |
| 6,251,136 B1 | 6/2001 | Guruwaiya et al. | |
| 6,293,959 B1 | 9/2001 | Miller et al. | |
| 6,309,402 B1 | 10/2001 | Jendersee et al. | |
| 6,335,029 B1 | 1/2002 | Kamath et al. | |
| 6,358,556 B1 | 3/2002 | Ding et al. | |
| 6,368,658 B1 | 4/2002 | Schwarz et al. | |
| 6,395,326 B1 * | 5/2002 | Castro et al. | 427/2.24 |
| 6,406,739 B1 | 6/2002 | LeBoeuf et al. | |
| 6,407,009 B1 | 6/2002 | You et al. | |
| 6,419,694 B1 | 7/2002 | Sandock | |
| 6,426,145 B1 | 7/2002 | Moroni | |
| 6,451,373 B1 | 9/2002 | Hossainy et al. | |
| 6,458,867 B1 | 10/2002 | Wang et al. | |
| 6,475,235 B1 | 11/2002 | Jayaraman | |
| 6,488,701 B1 * | 12/2002 | Nolting et al. | 623/1.13 |
| 6,503,954 B1 * | 1/2003 | Bhat et al. | 514/772.2 |
| 6,555,157 B1 | 4/2003 | Hossainy | |
| 6,574,497 B1 | 6/2003 | Pacetti | |
| 6,623,764 B1 | 9/2003 | Sokoll et al. | |
| 6,652,581 B1 | 11/2003 | Ding | |
| 6,723,373 B1 * | 4/2004 | Narayanan et al. | 427/2.25 |
| 6,739,033 B2 | 5/2004 | Hijlkema et al. | |
| 6,818,247 B1 | 11/2004 | Chen et al. | |
| 6,823,576 B2 | 11/2004 | Austin | |
| 6,948,223 B2 | 9/2005 | Shortt | |
| 7,077,859 B2 | 7/2006 | Sirhan et al. | |
| 7,291,165 B2 | 11/2007 | Rosenthal et al. | |
| 7,294,329 B1 * | 11/2007 | Ding | 424/1.65 |
| 7,504,125 B1 | 3/2009 | Pacetti et al. | |
| 2001/0018469 A1 * | 8/2001 | Chen et al. | 523/121 |
| 2002/0082685 A1 | 6/2002 | Sirhan et al. | |
| 2002/0127263 A1 | 9/2002 | Carlyle et al. | |
| 2005/0118344 A1 | 6/2005 | Pacetti | |
| 2005/0119720 A1 | 6/2005 | Gale et al. | |

FOREIGN PATENT DOCUMENTS

| | | |
|---|---|---|
| WO | WO 03/035131 | 5/2003 |
| WO | WO 03/082368 | 10/2003 |
| WO | WO 2005/004945 | 1/2005 |

OTHER PUBLICATIONS

EPO Examination Report for application 04 812 597.5-2307, mailed Sep. 6, 2007, 3 pgs.

EPO Examination Report for application 04 812 597.5-2307, mailed Jul. 4, 2008, 3 pgs.

International Search Report and Written Opinion for PCT/US2004/017060, filed May 28, 2004, mailed Dec. 30, 2004, 10 pgs.

International Search Report and Written Opinion for PCT/US2004/040121, filed Nov. 30, 2004, mailed Apr. 12, 2005, 12 pgs.

Perego et al., Copolymers of L and D,L Lactide with 6-caprolactone: synthesis and characterication, Malromol. Chem. 194, pp. 2463-2469 (1993).

The Random House College Dictionary, Rev. Ed. p. 375 (1982).

Van de Velde et al., "Biopolymers; overview of several properties and consequences on their applications", Polymer Testing, vol. 21, pp. 433-442 (2002).

* cited by examiner

METHOD OF DRYING BIOABSORBABLE COATING OVER STENTS

CROSS REFERENCE

This application is a continuation-in-part of U.S. application Ser. No. 10/856,984, now U.S. Pat. No. 7,807,211, which was filed on May 27, 2004, which is a continuation-in-part of U.S. application Ser. No. 10/603,794, now U.S. Pat. No. 7,682,647, which was filed on Jun. 25, 2003. This application is also a continuation-in-part of U.S. application Ser. No. 10/108,004, which was filed on Mar. 27, 2002. Now abandoned Furthermore, U.S. application Ser. No. 10/856,984 is also a continuation-in-part of U.S. application Ser. No. 10/304,360, now abandoned, which was filed on Nov. 25, 2002, which is a divisional of U.S. application Ser. No. 09/751,691, now U.S. Pat. No. 6,503,556 filed on Dec. 28, 2000. Additionally, U.S. application Ser. No. 10/856,984 is also a continuation-in-part of U.S. application Ser. No. 10/751,043 filed on Jan. 2, 2004, now abandoned which is a continuation of U.S. application Ser. No. 09/750,595 filed on Dec. 28, 2000. This application is also a continuation-in-part of U.S. application Ser. No. 12/363,538, now U.S. Pat. No. 8,007,858, which was filed on Jan. 30, 2009, which is a continuation of U.S. application Ser. No. 10/040,538, now U.S. Pat. No. 7,504,125, which was filed on Dec. 28, 2001, which is a continuation-in-part of U.S. application Ser. No. 09/894,293, filed on Jun. 27, 2001, now abandoned, which is a continuation-in-part of U.S. application Ser. No. 09/844,522, filed on Apr. 27, 2001, now U.S. Pat. No. 6,818,247. All of the aforementioned patent applications and patents are incorporated by reference herein.

BACKGROUND OF THE INVENTION

1. Field of the Invention

This invention relates to methods for coating stents.

2. Description of the State of the Art

This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent acute success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site. Delivery includes passing the stent through anatomical lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration that can produce adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of a stent with an active agent or an active agent and a polymeric carrier. Those of ordinary skill in the art fabricate coatings by applying a coating composition that includes a polymer, or a blend of polymers, to the stent using well-known techniques. Such a coating composition may include a polymer solution and an active agent dispersed in the solution. The composition may be applied to the stent by immersing the stent in the composition or by spraying the composition onto the stent. Removal of all or most of the solvent leaves on the stent surfaces a polymer coating impregnated with the drug or active agent.

SUMMARY OF THE INVENTION

Various embodiments of the present invention include: a method of coating a stent, comprising: applying a composition to a stent substrate, the composition including a polymer component and a solvent; exposing the polymer component to a temperature equal to or greater than a Tg of the polymer component, wherein the exposing removes solvent from the applied composition; and repeating the applying and exposing one or more times to form a coating, wherein the solvent content of the coating after the final exposing step is at a level suitable for a finished stent.

Further embodiments of the present invention include a method of coating a stent, comprising: applying a composition to a stent substrate, the composition including a polymer component and a solvent; thermally treating the applied composition, wherein the thermal treatment removes solvent from the applied composition; and repeating the applying and thermal treatment one or more times to form a coating, wherein a duration of each of the thermal treatments is less than 60 seconds (s).

Additional embodiments of the present invention include a method of making a stent, comprising: depositing a composition onto a stent substrate, the composition including a polymer component and a solvent; blowing a heated gas onto the deposited composition, wherein the heated gas removes solvent from the deposited composition; and repeating the applying and thermal treatment one or more times to form a coating, wherein the coating comprises less than 2 wt % solvent.

DETAILED DESCRIPTION OF THE INVENTION

Embodiments of the present invention relate to coating implantable medical devices such as stents. More generally, embodiments of the present invention may also be used in coating devices including, but not limited to, self-expandable stents, balloon-expandable stents, stent-grafts, vascular grafts, drug coated balloons, cerebrospinal fluid shunts, pacemaker leads, closure devices for patent foramen ovale, and synthetic heart valves. Even more generally, embodiments of the present invention may also be used for scaffolding or non-scaffolding purpose in the area of luminal application, vascular application, and correction, augmentation, fixing, and drug targeting of soft tissue and hard tissue.

In particular, a stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

In other embodiments, a metallic or polymeric filament or wire may also be coiled to form the stent. Filaments of polymer may be extruded or melt spun. These filaments can then be cut, formed into ring elements, welded closed, corrugated to form crowns, and then the crowns welded together by heat or solvent to form the stent.

Figure 1:
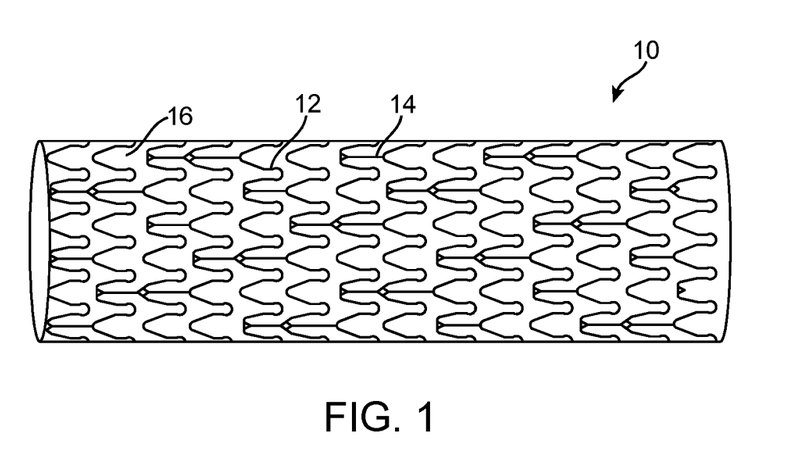
FIG. 1 depicts a three-dimensional view of a cylindrically-shaped stent.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

The cross-section of the struts in stent 10 may be rectangular- or circular-shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

Figure 2A:
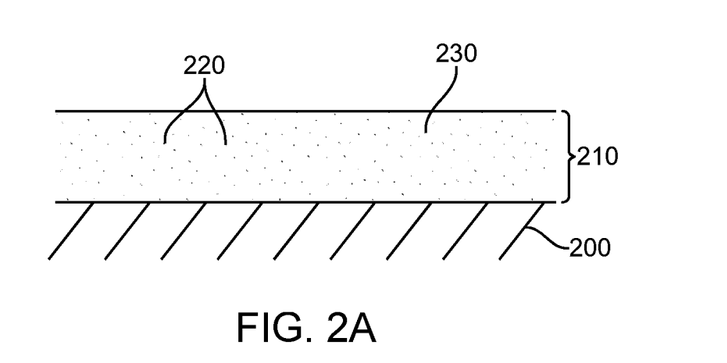
FIG. 2A depicts a cross-section of a stent surface with a drug-polymer layer.

A medicated stent may be fabricated by coating the surface of a stent with a drug. For example, a stent can have a coating including a drug dispersed in a polymeric carrier disposed over a substrate. FIG. 2A depicts a cross-section of a stent surface with a drug-polymer coating layer 210 over a substrate 200. In other embodiments, drug-polymer layer 210 can be disposed over a polymeric coating layer. In some embodiments, coating layer 210 can also be pure drug. Coating layer 210 includes a drug 220 dispersed in a coating polymer 230. As indicated above, a substrate or scaffolding can be metallic, polymeric, ceramic, or other suitable material.

Figure 2B:
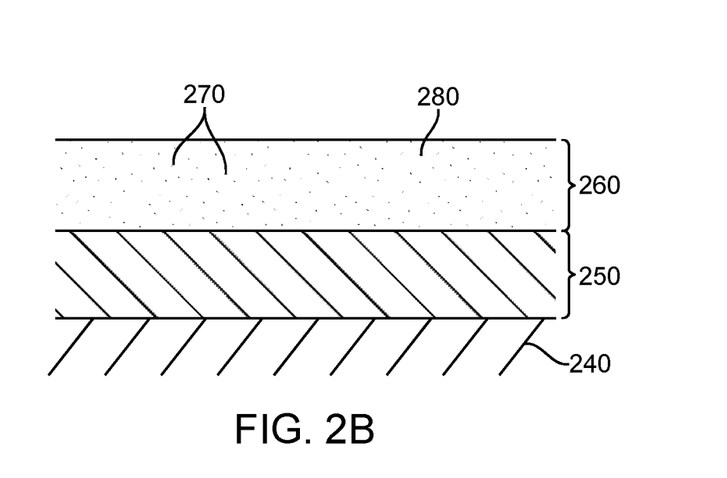
FIG. 2B depicts a cross-section of a stent surface with a primer layer and a drug-polymer layer.

FIG. 2B depicts a cross-section of a substrate 240 of a stent with a polymeric layer 250 disposed over substrate 240. A drug-polymer coating layer 260 is disposed over polymeric layer 250. Coating layer 260 includes a drug 270 dispersed within a polymer 280. Polymeric layer 250 can be a primer layer for improving the adhesion of drug-polymer layer 260 to substrate 240.

As indicated above, a coating on a stent may be formed by applying or depositing a coating composition including polymer dissolved in a solvent on the stent substrate, body, or scaffolding. The coating composition can optionally also include a therapeutic agent or drug or other substance, for example, a radiopaque agent.

The coating composition can be applied to a substrate by various methods, such as, dip coating, brushing, or spraying. The embodiments of the present invention are not limited to any particular application or deposition technique. In particular, spray coating a stent typically involves mounting or disposing a stent on a support, followed by spraying a coating composition from a nozzle onto the mounted stent. Solvent is removed from the deposited coating composition to form the coating. There typically is some residual solvent remaining in the coating after the solvent removal or solvent removal steps. As discussed in more detail below, solvent removal can be performed through evaporation at room or ambient temperature or with a thermal treatment that includes heating or exposing a coated stent to a temperature above room temperature. Room or ambient temperature may be between 20 and 30° C. and any temperature in between.

If a coating layer of a target thickness (or mass) is formed with a single application step and then followed by solvent removal, the coating layer that results can be nonuniform, include coating defects, or both. Stents, particularly those for coronary use, comprise an intricate stent pattern with small dimensions. If sufficient coating is applied all at once to load the desired amount of drug, the applied solution will form webs, pools, or strands in the stent pattern. Instead of the desired conformal coating, a highly non-uniform coating results. Therefore, a coating of a target thickness (or mass) is preferably formed with two or more cycles or passes of a coating composition application, such as spraying. After each cycle or pass, a solvent removal or drying step is performed. The solvent removal step after each pass is referred to as interpass drying. A cycle or pass refers to the application of a coating composition without an intervening solvent removal step, such as blowing warm air on the stent. In spraying, a cycle or pass can include directing the spray plume over the length of a stent one or more times. After each coating composition application pass, the application of coating composition on the substrate is stopped, which is followed by interpass solvent removal.

Figure 3:
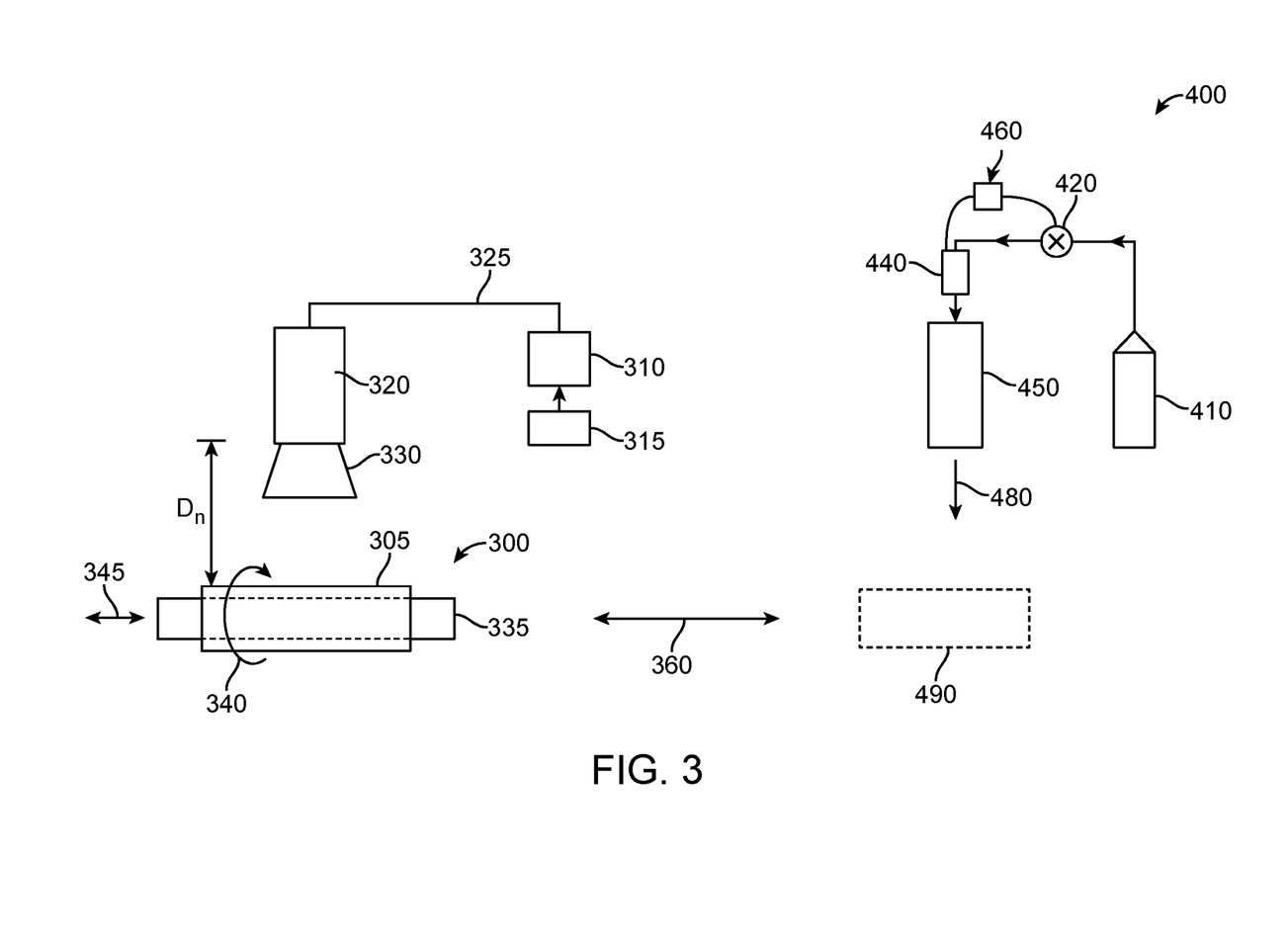
FIG. 3 depicts an exemplary schematic embodiment of an apparatus for spray coating a stent and in-process drying of the stent.

FIG. 3 depicts an exemplary schematic embodiment of an apparatus for spray coating a stent and in-process drying of the stent. During the coating process, a stent 305 is shifted back and forth between spray coating apparatus 300 and drying station 400. In spray coating apparatus 300, a syringe pump 310 pumps coating material from a reservoir 315 that is in fluid communication with a spray nozzle 320. Nozzle 320 can be in fluid communication with pump 310 through a tubing 325. Nozzle 320 provides a plume 330 of fine droplets of coating material for depositing on stent 305. Nozzle 320 is positioned a distance (Dn) from the surface of stent 305. A flow rate of coating material provided by pump 310 can be varied by changing the pump rate of pump 310.

Stent 305 is supported by a stent support 335, such as a mandrel. Support 335 can be configured to rotate stent 305 about its cylindrical axis, as shown by an arrow 340. Support 335 can also be configured to axially or linearly translate stent 305 with respect to plume 330, as shown by an arrow 345. As an alternative, nozzle 320 can be linearly translated with respect to stent 305. Further, both nozzle 320 and stent 305 can be simultaneously or independently linearly translated with respect to each other.

Stent 305 may pass nozzle/plume 320, 330 completely in one linear direction 345 to receive coating material, and then be directed in the reverse linear direction 345 past nozzle/plume 320, 330 to receive additional coating material.

As shown by arrow 360, stent 305 and support 335 are shifted to a position 490 to drying station 400. Drying station 400 includes a gas source 410, a flow controller 420 (e.g., a flow controller available from MKS Instruments, Wilmington, Mass.), an in-line heater 440 (e.g., an in-line heater available from Sylvania, Danvers, Mass.), a computer controller 460, and a nozzle 450. Computer controller 460 can be in communication with flow controller 420 and in-line heater 440 to control the amount of air and temperature, respectively, which is delivered to nozzle 450. In-line heater 440 can be used to precisely and gradually increase the temperature of the gas delivered by gas source 400 to the temperature used to conduct the drying. Nozzle 450 directs a heated gas stream 480 at stent 305 with applied coating material that is in position 490. Stent 305 and support 335 are shifted back to spray coating apparatus 300 for further coating application when the interpass drying step is completed.

The residual solvent content in the coating after interpass drying depends on factors such the coating formulation and the boiling point of the solvent. For a PDLLA-acetone formulation, the residual solvent content may be 4-7 wt % with no drying. For other formulations that include low volatility solvents, the solvent content could be as high as 10 wt %.

Each pass results in the formation of a coating layer of a given thickness that contains a residual amount of solvent. The multiple passes result in the formation of a coating composed of multiple layers, the combined thickness of the multiple layers being the target thickness of the coating. Any suitable number of repetitions of applying the composition followed by removing the solvent(s) can be performed to form a coating of a desired thickness or mass. Excessive application of the polymer can, however, cause coating defects.

As indicated above, interpass solvent removal, as used herein, also includes the solvent removal after the last coating composition application or last pass. Interpass solvent removal can be characterized as removal of solvent from a "wet" coating, wherein a wet coating refers to a deposited coating composition. After interpass solvent removal or drying of a wet coating layer, the coating may be characterized as a "dry" coating layer, although it contains residual solvent not removed by interpass drying.

After the final interpass coating composition application and interpass solvent removal, the dry coating may is typically subjected to a terminal solvent removal step to remove a significant portion of residual solvent. This terminal solvent removal step can be characterized as solvent removal from a dry coating. The terminal solvent removal treatment from the dry coating is typically significantly longer than the interpass solvent removal from the wet coating. Conventionally, the solvent removal from a dry coating is performed by baking the coated stent.

When spraying is used for application of coating composition, each pass or repetition can be, for example, about 0.5 second to about 20 seconds in duration. The amount of coating solids applied by each repetition can be about 1 microgram/cm$^2$ (of stent surface area) to about 100 micrograms/cm$^2$.

Interpass solvent removal results in a significant amount of the solvent(s) removed. For example, interpass solvent removal results a coating layer containing less than 5 wt %, 3 wt %, or more narrowly, less than 1 wt % of solvent remaining in the layer. The solvent content after terminal solvent removal depends on factors such the coating formulation and the boiling point of the solvent. For a PDLLA-acetone formulation, the residual solvent content may be less than 2 wt %. For other formulations that include low volatility solvents, the solvent content could be as high as 5 wt %.

Conventionally, the interpass solvent removal is not sufficient to reduce the residual solvent content of the coating to that of a finished coating. The shorter interpass solvent removal reduces process time, increasing manufacturing throughput, while allowing formation of a uniform multilayer coating. The duration of the terminal solvent removal process is significantly longer than the interpass drying in order to reduce the solvent content to the target solvent content.

Interpass solvent removal may be achieved by allowing the solvent to evaporate at room or ambient temperature. The time to remove solvent to a target solvent content depends in part on the volatility of the solvent. The solvent removal time for the interpass solvent removal can be decreased by subjecting the stent substrate with the applied coating composition to a thermal treatment process. Additionally, the terminal solvent removal can be achieved using a thermal treatment process.

A thermal treatment process includes exposing the stent substrate with applied coating composition, in the case of interpass drying, or the stent substrate with a coating having residual solvent, to a temperature greater than room or ambient temperature. A thermal treatment process can include blowing a heated gas on the stent substrate with the coating composition or coating. The thermal treatment process can also include baking the stent substrate with the applied coating composition or coating with residual solvent in an oven. A typical process includes used the heated gas for interpass solvent removal and baking for the terminal solvent removal.

In the heated gas interpass solvent removal, the stent may be positioned below a nozzle blowing the heated or warm gas. By way of example, warm gas applications can be performed at a flow speed of less than about 5,000 feet/minute, and for about 10 seconds. The gas can be directed onto the stent following a waiting period of about 0.1 second to about 5 seconds after the application of the coating composition so as to allow the liquid sufficient time to flow and spread over the stent surface before the solvent(s) is removed to form a coating. The waiting period is particularly suitable if the coating composition contains a volatile solvent since such solvents are typically removed quickly. As used herein "volatile solvent" means a solvent that has a vapor pressure greater than 17.54 Torr at ambient temperature, and "non-volatile solvent" means a solvent that has a vapor pressure less than or equal to 17.54 Torr at ambient temperature. In terminal solvent removal, a stent is typically dried in an oven as the final drying step when the deposition stages are completed. The time for solvent removal is typically much longer than interpass solvent removal. For example, a stent can be baked in an oven at a mild temperature (e.g., 40-50° C.) for a suitable duration of time (e.g., 30 min-4 hours) or by the application of warm air.

Various embodiments of the present invention include performing the interpass drying in a manner that provides a target solvent content in the coating with reduced terminal solvent removal time or no terminal solvent removal, for example, no baking step. There are significant advantages to reducing the time of or eliminating the terminal solvent removal step. First, such embodiments will improve the production throughput and reduce the equipment and labor costs due to the removal of the baking step. Second, the risk of adverse effects on the surface and bulk properties on the polymer of the coating and polymer substrate from prolonged baking will be reduced or eliminated. Third, there is a benefit in knowing the final "dry" stent weight immediately following the spray/dry process. Spray process corrections can happen more quickly and with improved accuracy by having the dry stent weight immediately rather than having the weight 30-60 min after the coating, a typical time for terminal drying in an oven.

The second advantage is particularly important for stents having bioabsorbable polymer substrates over which coatings are formed and also for bioabsorbable polymer coatings over both polymer and metallic substrates. Bioabsorbable polymer substrates are designed to provide mechanical support to lumen walls for a period of time and then degrade and dissolve away from the implant site. The mechanical and degradation properties can be sensitive to exposure to elevated temperatures for prolonged periods. Additionally, the surface and degradation properties of bioabsorbable polymeric coatings can also be sensitive to the prolonged exposure to elevated temperatures of a terminal solvent removal step, such as baking. Preserving the surface and bulk properties of the bioabsorbable coating and stent materials are critical to the overall performance of the stent.

Exemplary polymers that can be used as a bioabsorbable substrate or in a coating include, but are not limited to, poly (L-lactide) (PLLA), poly(D,L-lactide) (PDLA), and polyglycolide (PGA). Random or alternating copolymers or block copolymers of the above polymers with each other or other polymers may also be used, for example, poly (D,L-lactide-co-glycolide), and poly(L-lactide-co-glycolide) (PLGA). For PLGA, any molar proportion of L-lactide to glycolide is included, such as, 90:10, 75:25, 50:50, 25:75, and 10:90.

As shown in Table 1 below, the above polymers have glass transition temperatures (Tg) above room or ambient temperature. PLLA, PDLA, and a wide range of PLGA compositions have a Tg above human body temperature. Human body temperature is approximately 37° C. These Tgs are for the polymers with minimal solvent content (<1% w/w) and a moisture content in equilibrium with typical ambient conditions. The Tg range for PGA is above and below human body temperature.

TABLE 1

Glass transition temperatures and melting points of polymers.

| Polymer | Melting Point (° C.)[1] | Glass-Transition Temp (° C.)[1] |
|---|---|---|
| PGA | 225-230 | 35-40 |
| PLLA | 173-178 | 60-65 |
| PDLA | Amorphous | 55-60 |
| 85/15 PLGA | Amorphous | 50-55 |
| 75/25 PLGA | Amorphous | 50-55 |
| 65/35 PLGA | Amorphous | 45-50 |
| 50/50 PLGA | Amorphous | 45-50 |

[1]Medical Plastics and Biomaterials Magazine, March 1998.

The substrate and coatings can also be made from random or alternating or block copolymers of the above polymers with polymers having Tg's below room or body temperature including, but not limited to, polycaprolactone (PCL), poly (trimethylene carbonate) (PTMC), polydioxanone (PDO), poly(4-hydroxy butyrate) (4-PHB), poly(3-hydroxybutyrate) (3-PHB), and poly(butylene succinate) (PBS).

An exemplary stent includes a stent substrate or backbone made of PLLA and a coating that includes Everolimus drug and PDLA polymer, for example, with a 1:1 weight ratio. The coating for this stent can be formed by methods of the present invention. The coating composition (4 wt % drug and polymer in acetone, drug to polymer ratio of 1:1) is sprayed over the stent.

A coating process includes an interpass or inprocess dry station. A conventional coating process includes an interpass drying and a final oven bake. The interpass drying is 15 seconds per dry cycle at 40° C. to remove most of the solvent from the coating and a final oven bake at 50° C. with the oven time at 30 to 60 minutes.

In this conventional process, a two-stage weight loss profile of the residual solvent from the coating has been observed when a coated stent is baked in an oven. In the first stage, the weight vs. time decreases steeply, corresponding to a rapid loss of residual solvent. The weight vs. time then levels off gradually after a few minutes and in a second stage, the weight decreases gradually during the remainder of the oven bake. The evaporation rate of the solvent in the first stage is believed to be governed by several variables including surface to volume ratio, vapor pressure, surface temperature, and air flow over the surface.

During the second stage, it is believed that the solvent loss is dependent primarily on the rate of diffusion of the solvent molecules through the coating. The diffusion rate is primarily controlled by the free volume availability of the polymer. The diffusion mechanism is believed to be the solvent molecules jumping from one free volume hole to another. In such a mechanism, it is believed that the most important factor in affecting the free volume is the temperature difference between the processing temperature of the thermal treatment (e.g., baking temperature) (Tp) and the Tg of the polymer of the coating material (Tp–Tg).

As indicated above, embodiments of the present invention include performing the interpass drying in a manner that provides a target solvent content in the coating with reduced terminal solvent removal time or no terminal solvent removal, for example, no baking step. In some embodiments, the target solvent content in the coating after the final interpass drying step is at a level suitable for a finished stent. In other embodiments, the target solvent content in the coating after a reduced terminal solvent removal time (e.g., baking time) is at a level suitable for a finished stent.

In embodiments of the invention, a coating composition is applied to a stent substrate that includes a polymer in a solvent. Certain embodiments of the present invention include performing at least one interpass solvent removal step with a thermal treatment in which a target temperature is greater than or equal to the Tg of the polymer of the coating. An interpass thermal treatment includes heating or exposing a polymer of the applied composition to a target or process temperature. In some embodiments, the process temperature for all or each of the interprocess solvent removal steps is greater than or equal to the Tg of the polymer of the coating composition.

In certain embodiments, the interpass thermal treatment includes heating to or exposure of the coating to the target or process temperature for a process time between 0-5 s, 0-10 s, 0-30 s, 0-60 s, 0-2 min, or less than 5 min. In other embodiments, the process time is between 0-5 s, 5-10 s, 10-15 s, 15-30 s, 30-60 s, 60 s-2 min, or 2-5 min. In additional embodiments, the process time is less than 5 s, 10 s, 15 s, 30 s, 60 s, 2 min, or 5 min. The thermal treatment in a preferred embodiment is blowing a warm gas on the stent. In this preferred embodiment, the blowing of the warm gas on the stent is performed for one of the above time periods.

In some embodiments, the polymer has a Tg greater than room temperature. In other embodiments, the polymer also has a Tg greater than human body temperature. In additional embodiments, the polymer is a block copolymer having at least one block with a Tg greater than room temperature or additionally greater than human body temperature. In this case, the thermal treatment temperature of the interpass solvent removal is greater than the Tg of the block or all blocks having a Tg greater than room or also human body temperature.

In further embodiments, a stent fabrication process including two or more coating composition application steps and a corresponding interpass solvent removal thermal treatment includes a terminal solvent removal step, such as baking, for less than 30 min, less than 20 min, less than 10 min, less than 5 min, or less than 2 min. The terminal solvent removal step may be 20-30 min, 10-20 min, 5-10 min, or 2-5 min. In such embodiments, no additional solvent removal step is performed after the terminal solvent removal step. Alternatively, no additional thermal treatment involving exposure of the stent to temperature greater than 40° C. is performed. Alternatively or additionally, no additional thermal treatment involving exposure for greater than 30 s, 60 s, 2 min, or greater than 5 min is performed on the stent.

In other embodiments, no terminal solvent removal step, such as baking, is performed after the last interpass solvent removal step in a stent fabrication process including two or more coating composition application steps and a corresponding interpass solvent removal thermal treatment. In such embodiments, no additional solvent removal step may be performed after the final interpass solvent removal step. Alternatively, no additional thermal treatment involving exposure of the stent to a temperature greater than 40° C. is performed. Alternatively or additionally, no additional thermal treatment involving exposure for greater than 30 s, 60 s, 2 min, or greater than 5 min is performed on the stent.

The target solvent content of the coating after the last interpass solvent removal step or after the reduced duration terminal solvent removal step may be less than 5 wt %, 4 wt %, 3, wt %, 2 wt %, 1 wt %, or less than 0.05 wt % of the coating. Additionally, the target solvent content of the coating after the last interpass solvent removal step may be 0.05-1 wt %, 1-2 wt %, 2-3 wt %, 3-4 wt %, and 4-5 wt % of the coating.

The process temperature for interpass drying may be Tg or slightly above Tg or more. For example, Tp–Tg may be less than 1° C., 3° C., 5° C., 7° C., 10° C., 12° C., 15° C., or less than 20° C. Additionally, the Tp–Tg may be 1-3° C., 3-5° C., 5-7° C., 7-10° C., 10-12° C., 12-15° C., or 15-20° C. In addition, the process temperature can be any temperature or range that is above Tg and also between room temperature and 90° C. The upper limit of the process temperature may be limited by considerations such as degradation of a drug in the coating, degradation of the coating polymer, or degradation of properties of the substrate polymer. Drugs with a propensity to oxidation typically start to degrade between 80-100° C., so the process temperature should less than this range. However, there may be drugs which start to degrade at temperatures higher than this range, thus a higher process temperature may be used.

The amount of solvent removal, and thus, the solvent content of the coating after interpass drying depends on both the process time and temperature. In general, the longer the process time, the higher the process temperature, or both, the greater the solvent removal and lower the solvent content of the coating. Embodiments of the invention include, a process time and temperature combination and selection thereof that provides a target solvent content of the coating, such as the values and ranges of target solvent content disclosed herein. Any combination of the process time and temperature values or ranges are embodiments of the invention. It is neither known or predictable that there exist combinations of process time and temperature that can provided particular desired target solvent content of a coating with a reduced terminal thermal treatment (e.g., reduced baking time) or no terminal thermal treatment (e.g., no baking).

In the interpass drying, the stent may be positioned below a nozzle blowing the warm gas. A warm gas may be particularly suitable for embodiments in which the solvent employed in the coating composition is a non-volatile solvent (e.g., dimethylsulfoxide (DMSO), dimethylformamide (DMF), and dimethylacetamide (DMAC)).

Any suitable gas can be employed, examples of which include air, argon, or nitrogen. The flow rate of the warm gas can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm gas can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds.

A spray apparatus, such as EFD 780S spray device with VALVEMATE 7040 control system (manufactured by EFD Inc., East Providence, R.I., can be used to apply a composition to a stent. A EFD 780S spray device is an air-assisted external mixing atomizer. The composition is atomized into small droplets by air and uniformly applied to the stent surfaces. Other types of spray applicators, including air-assisted internal mixing atomizers and ultrasonic applicators, can also be used for the application of the composition.

To facilitate uniform and complete coverage of the stent during the application of the composition, the stent can be rotated about the stent's central longitudinal axis. Rotation of the stent can be from about 0.1 rpm to about 300 rpm, more narrowly from about 30 rpm to about 200 rpm. By way of example, the stent can rotate at about 150 rpm. The stent can also be moved in a linear direction along the same axis. The stent can be moved at about 1 mm/second to about 12 mm/second, for example about 6 mm/second, or for a minimum of at least two passes (i.e., back and forth past the spray nozzle).

A nozzle can deposit coating material onto a stent in the form of fine droplets. An atomization pressure of a sprayer can be maintained at a range of about 5 psi to about 30 psi. The droplet size depends on factors such as viscosity of the solution, surface tension of the solvent, atomization pressure, and flow rate. The flow rate of the composition from the spray nozzle can be from about 0.01 mg/second to about 1.0 mg/second, for example about 0.1 mg/second. Only a small percentage of the composition that is delivered from the spray nozzle is ultimately deposited on the stent. By way of example, when a composition is sprayed to deliver about 1 mg of solids, only about 100 micrograms or about 10% of the solids sprayed will likely be deposited on the stent.

A non-polymer substrate for an implantable medical device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

In accordance with one embodiment, the coating material can include a solvent and a polymer dissolved in the solvent and optionally a wetting fluid. The coating material can also include active agents, radiopaque elements, or radioactive isotopes. Representative examples of polymers that may be used as a substrate of a stent or coating for a stent, or more generally, implantable medical devices include, but are not limited to, poly (N-acetylglucosamine) (Chitin), Chitosan, poly(3-hydroxyvalerate), poly(L-lactide-co-glycolide), poly (3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly (L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly (vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and combinations thereof.

A "wetting" of a fluid is measured by the fluid's capillary permeation. Capillary permeation is the movement of a fluid on a solid substrate driven by interfacial energetics. Capillary permeation is quantified by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of the wetting fluid include, but are not limited to, tetrahydrofuran (THF), methanol, dimethylformamide (DMF), 1-butanol, n-butyl acetate, dimethylacetamide (DMAC), and mixtures and combinations thereof.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, 40-O-tetrazole-rapamycin ABT-578, biolimus, deforolimus, temsirolimus, myolimus, and novolimus.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

EXAMPLE

The following example illustrates interpass drying with no baking step and the influence of thermal treatment temperature and treatment duration on solvent removal from a bioabsorbable coating over a bioabsorbable stent substrate. The stent substrate was PLLA and the coating is a 1:1 ratio by weight of Everolimus drug and PDLA polymer (Tg is about 55 to about 60° C.). The coating composition was 4 wt % drug and polymer in acetone, 1/1 drug to polymer, which was sprayed over the stent substrate. In between coating composition applications, the applied composition is heated in an in-process dry station to remove solvent from the applied coating composition. A heated gas is blown onto the stent at the interpass dry station.

Table 2 lists the residual acetone level of the coated stent at various interpass dry temperatures and interpass dry times. The first two rows, Group 7, is the Control which represents results of the solvent removal that includes both interpass drying and baking The first row represents solvent removal at the interpass dry station with a temperature of 40° C., below the Tg of the coating polymer. At the end of the coating application passes, the stent is baked at 50° C. for 30 minutes. Groups 1 to 6 are the results for interpass drying without any oven bake at three different temperatures and two treatment durations per temperature.

Figure 4:
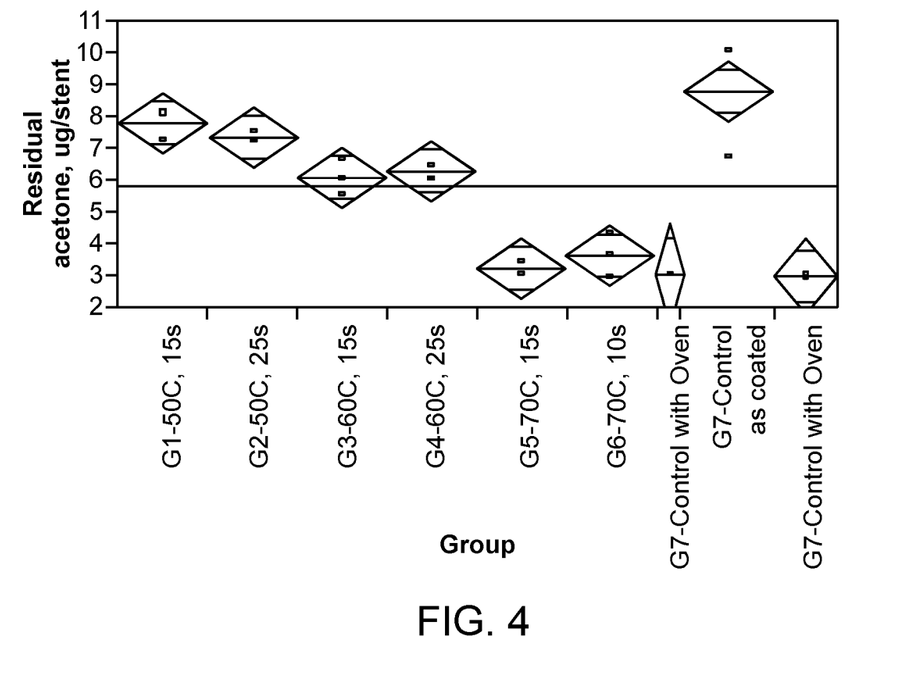
FIG. 4 depicts the acetone residual level on as coated stent at different interpass drying and control conditions.

FIG. 4 and Table 2 show the acetone residual level on as coated stents at different interpass drying and control conditions. As shown in FIG. 4 and Table 2, the interpass dry temperature at 70° C. and interpass dry time 10 seconds (Group 6) achieves the same acetone residual level (See FIG. 4) as the Control. Thus, interpass drying above Tg of the coating polymer can replace the Control process that uses a combination of interpass drying and an oven bake step, both below Tg of the coating polymer. The final acetone level of the Group 6 finished product is well within the target specification. No additional drug (Everolimus) degradation was detected from this study using the elevated interpass dry temperatures between 50 and 70° C.

TABLE 2

Results for solvent removal at various temperatures and times.

| Study Group (n = 3) | Average residual acetone, µg/stent | Average residual acetone, % |
| --- | --- | --- |
| Group 7-Control (as coated, 40° C. 15 s) | 8.8 ± 1.8 | 2.5 |
| Group 7-Control (with 50° C. oven/ 30 min) | 3.0 ± 0.1 | 0.9 |
| Group 1 (50° C./15 seconds) | 7.8 ± 0.5 | 2.2 |
| Group 2 (50° C./25 seconds) | 7.3 ± 0.2 | 2.2 |
| Group 3 (60° C./15 seconds) | 6.0 ± 0.6 | 1.8 |
| Group 4 (60° C./25 seconds) | 6.3 ± 0.21 | 1.9 |
| Group 5 (70° C./15 seconds) | 3.2 ± 0.2 | 1.0 |
| Group 6 (70° C./10 seconds) | 3.6 ± 0.7 | 1.0 |

Figure 5:
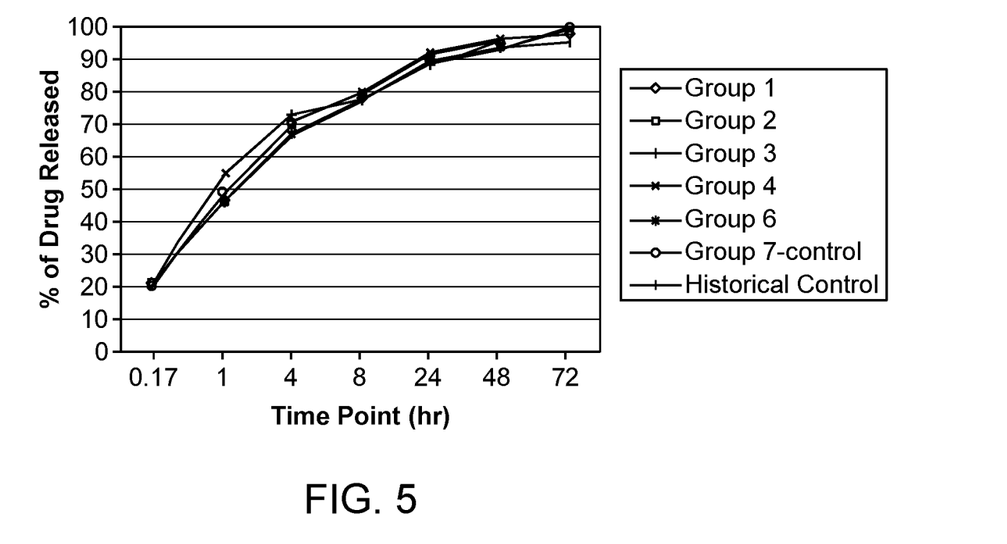
FIG. 5 depicts drug release profiles.

FIG. 5 depicts drug release profiles for Groups in Table 2. The drug release profiles and rates were very similar among the groups.

Thus, by drying the coating at a temperature slightly above the Tg of the material, the drying rate can be improved significantly since the lengthy oven bake step is eliminated. Elimination of baking step decreases process time and reduces manufacturing cost.

Other potential benefits of removing the oven bake step include reducing the heat exposure time of the substrate material which may allow it to better retain its properties, decrease equipment cost (e.g. eliminate oven and pre-bake balances), decrease direct labor, decrease yield loss incurred in oven-bake step, and decrease batch loss due to power outage.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:
1. A method of coating a stent, comprising:
   applying a composition to a stent substrate, the composition including a polymer component and a solvent;
   exposing the polymer component to a temperature equal to or greater than a Tg of the polymer component, wherein the exposing removes solvent from the applied composition, wherein the exposing comprises blowing a heated gas on the polymer component to heat the polymer component to a temperature equal to or greater than the Tg of the polymer component; and repeating the applying and exposing one or more times to form a coating, wherein the solvent content of the coating after the final exposing step is at a level suitable for a finished stent.

2. The method of claim 1, wherein the Tg of the polymer component is greater than room temperature.

3. The method of claim 1, wherein the Tg of the polymer component is greater than human body temperature.

4. The method of claim 1, wherein the stent substrate is a bioabsorbable polymer.

5. The method of claim 1, wherein the polymer component is a bioabsorbable polymer.

6. The method of claim 1, wherein the stent substrate is poly(L-lactide (PLLA) and the polymer component is poly(DL-lactide) (PDLA), the composition and the coating further comprising a therapeutic agent.

7. A method of coating a stent, comprising:
applying a composition to a stent substrate, the composition including a polymer component and a solvent, wherein the composition is uniformly applied to surfaces of the stent substrate;
thermally treating the applied composition, wherein the thermal treatment removes solvent from the applied composition; and
repeating the applying and thermal treatment one or more times to form a coating,
wherein a duration of each of the thermal treatments is less than 60 s,
wherein the polymer component is a bioabsorbable polymer.

8. The method of claim 7, wherein the stent substrate is a bioabsorbable polymer.

9. The method of claim 7, wherein the thermal treatment comprises blowing a heated gas on the stent.

10. The method of claim 7, wherein the solvent content of the coating is reduced to less than 2 wt% by the thermal treatment.

11. A method of coating a stent, comprising:
applying a composition to a stent substrate, the composition including a polymer component and a solvent, wherein the composition is uniformly applied to surfaces of the stent substrate;
thermally treating the applied composition, wherein the thermal treatment removes solvent from the applied composition; and
repeating the applying and thermal treatment one or more times to form a coating,
wherein a duration of each of the thermal treatments is less than 60 s,
wherein the stent is not baked after the final repetition of the thermal treatment.

12. A method of coating a stent, comprising:
applying a composition to a stent substrate, the composition including a polymer component and a solvent, wherein the composition is uniformly applied to surfaces of the stent substrate;
thermally treating the applied composition, wherein the thermal treatment removes solvent from the applied composition; and
repeating the applying and thermal treatment one or more times to form a coating,
wherein a duration of each of the thermal treatments is less than 60 s,
wherein no additional thermal treatment of the stent is performed after the final repetition of the thermal treatment.

13. A method of coating a stent, comprising:
applying a composition to a stent substrate, the composition including a polymer component and a solvent, wherein the composition is uniformly applied to surfaces of the stent substrate;
thermally treating the applied composition, wherein the thermal treatment removes solvent from the applied composition; and
repeating the applying and thermal treatment one or more times to form a coating,
wherein a duration of each of the thermal treatments is less than 60 s,
wherein the thermal treatment comprises exposing the polymer component to a temperature equal to or greater than a Tg of the polymer component.

14. A method of coating a stent, comprising:
applying a composition to a stent substrate, the composition including a polymer component and a solvent, wherein the composition is uniformly applied to surfaces of the stent substrate;
thermally treating the applied composition, wherein the thermal treatment removes solvent from the applied composition; and
repeating the applying and thermal treatment one or more times to form a coating,
wherein a duration of each of the thermal treatments is less than 60 s,
wherein no additional thermal treatment involving exposure of the stent to a temperature greater than 40° C. is performed or no additional thermal treatment involving exposure for greater than 60 s is performed on the stent.

15. A method of coating a stent, comprising:
depositing a composition onto a stent substrate, the composition including a polymer component and a solvent, wherein the composition is uniformly deposited to surfaces of the stent substrate;
blowing a heated gas onto the deposited composition, wherein the heated gas removes solvent from the deposited composition; and
repeating the applying and thermal treatment one or more times to form a coating, wherein the coating comprises less than 2 wt% solvent,
wherein further processing steps do not include baking the stent to remove residual solvent.

16. The method of claim 15, wherein the heated gas is nitrogen to create an inert blanket.

17. The method of claim 15, wherein the heated gas is applied in a pulsed sequence.

* * * * *

UNITED STATES PATENT AND TRADEMARK OFFICE
CERTIFICATE OF CORRECTION

| | | Page 1 of 1 |
|---|---|---|
| PATENT NO. | : 8,632,845 B2 | |
| APPLICATION NO. | : 12/766758 | |
| DATED | : January 21, 2014 | |
| INVENTOR(S) | : Chen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 752 days.

Signed and Sealed this
Nineteenth Day of May, 2015

Michelle K. Lee
*Director of the United States Patent and Trademark Office*